(12) United States Patent  (10) Patent No.: US 6,608,277 B2
Spooner et al.  (45) Date of Patent: Aug. 19, 2003

(54) AUTOMATED BRACHYTHERAPY SEED PRODUCTION SYSTEM

(75) Inventors: Scott A. Spooner, Trophy Club, TX (US); Tommy L. Thompson, Denton, TX (US); Michael L. Vinson, Denton, TX (US)

(73) Assignee: Bard Acquisition Sub. Inc., Murray Hill, NC (US)

( * ) Notice: Subject to any disclaimer, the term of this patent is extended or adjusted under 35 U.S.C. 154(b) by 0 days.

(21) Appl. No.: 10/171,523

(22) Filed: Jun. 11, 2002

(65) Prior Publication Data

US 2002/0162828 A1 Nov. 7, 2002

Related U.S. Application Data

(62) Division of application No. 09/569,536, filed on May 12, 2000, now Pat. No. 6,403,916.

(51) Int. Cl.[7] .............................................. B23K 26/00
(52) U.S. Cl. ........................... 219/121.63; 219/121.15; 219/121.76
(58) Field of Search ..................... 219/121.63, 121.15, 219/121.76, 121.83, 59.1

(56) References Cited

U.S. PATENT DOCUMENTS

| | | | | |
|---|---|---|---|---|
| 3,048,701 A | * | 8/1962 | Thomas | 250/106 |
| 3,085,155 A | * | 4/1963 | Kern et al. | 250/71.5 |
| 3,476,939 A | * | 11/1969 | Goodman et al. | 250/106 |
| 3,488,495 A | * | 1/1970 | Schneeman | 250/52 |
| 4,323,055 A | * | 4/1982 | Kubiatowicz | 128/1.2 |
| 4,496,819 A | | 1/1985 | Acker et al. | |
| 4,511,426 A | | 4/1985 | Linner | |
| 4,694,137 A | | 9/1987 | Hawkins et al. | |
| 4,702,228 A | * | 10/1987 | Russell, Jr. et al. | 128/1.2 |
| 4,891,165 A | * | 1/1990 | Suthanthiran | 252/633 |
| 4,994,013 A | * | 2/1991 | Suthanthiran et al. | 600/8 |
| 5,073,694 A | | 12/1991 | Tessier et al. | |
| 5,405,309 A | | 4/1995 | Carden, Jr. | |
| 5,464,963 A | * | 11/1995 | Hostler et al. | 219/121.82 |
| 5,620,625 A | | 4/1997 | Sauron et al. | |
| 5,643,477 A | * | 7/1997 | Gullo et al. | 219/121.86 |
| 5,713,828 A | | 2/1998 | Coniglione | |
| 5,904,864 A | | 5/1999 | Nester et al. | |
| 5,921,459 A | * | 7/1999 | Heraly et al. | 228/45 |
| 5,968,380 A | * | 10/1999 | Hayashi et al. | 219/121.64 |
| 5,997,463 A | * | 12/1999 | Cutrer | 600/8 |
| 6,163,947 A | * | 12/2000 | Coniglione | 29/458 |
| 6,196,964 B1 | | 3/2001 | Loffler et al. | |

FOREIGN PATENT DOCUMENTS

DE 4425861 1/1996
JP 9250972 9/1997

OTHER PUBLICATIONS

Abstract: DE 4425861, Spemaba Spezialmaschbau GMGH Pluten, Jan. 25, 1994.
Abstract: JP 9250972, Futaku Seimitsu Kikai Kogyo KK, Sep. 1997.

\* cited by examiner

Primary Examiner—M. Alexandra Elve
(74) Attorney, Agent, or Firm—Stroock & Stroock & Lavan LLP

(57) ABSTRACT

An automated system, method and apparatus for producing welded end closures in thin-walled metal tubes, preferably sealing a radioactive source inside the tubes, by use of an electronically controlled robot that grasps and sequentially repositions the tube through a series of stations in which the tube is bottom-welded, inspected, filled, inspected, top welded and inspected, and wherein the tube bottom and top are welded using multi-directional laser beams generated by a single laser light source and discharged through a plurality of spaced-apart laser welder heads. Brachytherapy seeds containing radiolabeled microspheres are produced using the system, method and apparatus of the invention.

7 Claims, 6 Drawing Sheets

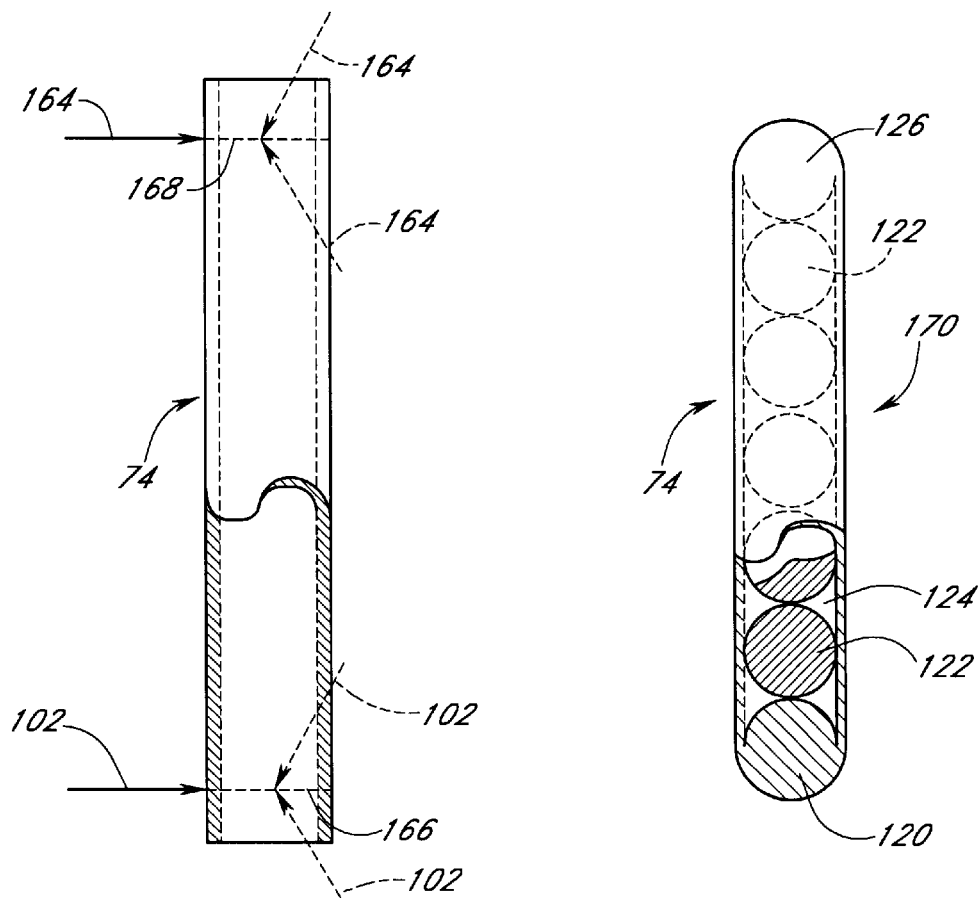
FIG. 9
FIG. 10
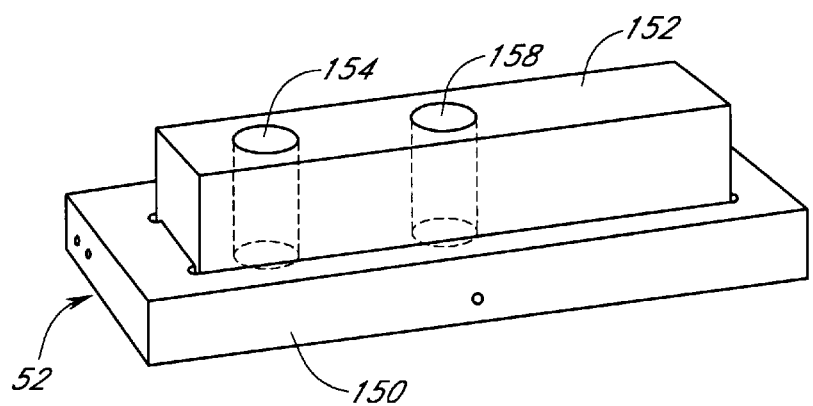
FIG. 11

AUTOMATED BRACHYTHERAPY SEED PRODUCTION SYSTEM

This application is a divisional application of U.S. patent application Ser. No. 09/569,536 filed on May 12, 2000 now U.S. Pat. No. 6,403,916, the disclosure of which is incorporated in its entirety herein by reference.

BACKGROUND OF THE INVENTION

1. Technical Invention

This invention relates to a system and method for laser welding the ends of thin-walled metal tubes and, optionally, for filling and sealing a contained mass inside the metal tubes by use of a robot and a multidirectional laser. More particularly, the invention relates to a system and method for manufacturing radioactive brachytherapy "seeds" that are implantable for use in medical therapy such as the irradiation of tumors.

2. Prior Art

The use of radiation therapy in medicine, particularly in cancer treatment, is well established. Conventional external radiation sources are used to irradiate both cancer tumor bodies and residual cancerous tissues after surgical excision of a solid tumor. Irradiation utilizing exterior radiation sources is limited in usefulness due to the high doses of radiation required and the resultant harmful consequences to surrounding and intervening healthy tissues.

Interstitial brachytherapy (short-range therapy) is also a well-established medical procedure in which a source of radioactivity, often called a "seed," is implanted within or near a tumor or other tissue. This procedure produces more focused radiation dosages and reduces the total radiation dosage required to achieve a desired therapeutic effect, thereby reducing harm to surrounding normal tissues. The seed is generally a hollow, sealed container made of a material that is relatively transparent to radiation. The radiation source within the seed varies with the required medical specifications, the type of radioisotope and the manufacturing process.

Examples of brachytherapy seeds are disclosed in U.S. Pat. No. 4,891,165 to Suthanthrian, U.S. Pat. No. 4,323,055 to Kubiatowicz, U.S. Pat. No. 4,702,228 to Russell, U.S. Pat. No. 5,405,309 to Carden, and U.S. Pat. No. 5,997,463 to Cutrer.

Suthanthrian discloses a brachytherapy seed comprising two hollow cylinders, each having one open end. One cylinder is slightly smaller than the other, allowing the open end of the first to slide into and toward the closed end of the second cylinder. The cylinders desirably fit together tightly.

Kubiatowicz discloses a seed construct wherein the radioactive material is loaded manually and the ends of the titanium seed are welded shut such as by plasma-arc welding.

Russell and Carden disclose the same seed construct, which improves on the Kubiatowicz and Suthanthrian seeds by using form-fitting caps at the ends of a hollow cylindrical titanium seed. These caps are laser welded onto the cylinder body. This configuration produces seed ends that are the same thickness as the walls. While this diminishes the anisotropy of the emitted radiation relative to the Kubiatowicz and Suthanthrian seeds, the cap-cylinder overlap creates a zone of thicker seed material that causes some anisotropy in the emitted radiation.

Cutrer discloses a brachytherapy source and method of manufacture in which a single laser and a rotating chuck are used, either alone or in combination with crimping, to seal radioactive spheres inside metal tubes. The laser is preferably activated in four series of short pulses to complete the welds because welding with a single laser can produce an unstable weld pool that can interfere with sealing and with the radiation pattern exhibited by the resultant product. Cutrer also discloses the provision of an inert gas source to minimize or eliminate oxidation during welding and to cool the weld afterwards.

The prior art construction of brachytherapy seeds also involves manual addition of the radiation source and sealing the seed in a separate, discontinuous step. This manufacturing scheme is labor intensive, time consuming and results in significant radiation exposure to workers. Additionally, the Food and Drug Administration and the Nuclear Regulatory Commission require the radioactive materials to be safely contained so as to prevent leakage and radiation poisoning.

A safe, automated method and apparatus that will facilitate the manufacture of brachytherapy seeds while minimizing worker radiation exposure, improving product quality and increasing manufacturing capacity are therefore needed.

SUMMARY OF THE INVENTION

This invention disclosed herein is an automated system and method useful for producing welded end closures in thin-walled metal tubes, and for encapsulating or containing a mass within a small-diameter metal tube. As used herein, the term "thin-walled" generally refers to tubes having wall thicknesses less than about 0.5 mm. The encapsulated mass can comprise a solid, liquid or gel, and, as more particularly described below, can comprise a radioactive component to facilitate use in biomedical applications. According to a particularly preferred embodiment of the invention, the small-diameter, thin-walled, metal tubes used in the invention are made of titanium, the mass includes a plurality of radiolabeled spherical metal bodies, and encapsulation or containment is achieved by laser welding the bottom and top ends of the metal tube using a multi-directional laser source to produce brachytherapy seeds.

The system of the invention preferably comprises a plurality of discrete modules or subassemblies serviced by a SCARA-form robot mounted on a stationary base, all housed inside a protective enclosure such as a sealed, negative pressure isolation glove box, which maintains a filtered production environment and provides containment and shielding for any radioactive component of the product. The discrete modules of the system contained inside the enclosure preferably include the SCARA robot, an automated gripper, a tube dispenser, a multi-directional laser welder, a loader-filler, at least one inspection module, and an output receiver. "SCARA" is commonly used to refer to a robot having a "Selectively Compliant Articulated Robot Arm." SCARA robots have a cylindrical work envelope, and the articulated support arm permits access to work locations disposed at virtually all locations within the envelope.

The subject system is desirably automated and operated by programmable electronic controllers that cause the various modules to perform functions as disclosed herein, sometimes receiving input from, and sometimes directing signals to, a plurality of sensors and transducers. One primary control computer preferably receives feedback from the robot and various other sensing devices to control the process. A second computer desirably provides information regarding fine visual positioning at the laser welder to the primary control computer.

According to a particularly preferred embodiment of the invention, the laser welder comprises three laser outputs spaced at even intervals around a target location and positioned so that beams routed from a common source through a splitter and fiber optic cables converge in a target zone at substantially the same time to weld the selected end of a metal tube while the tube is held in position by the automated gripper of the robot.

According to a preferred embodiment of the method of the invention, precut metal tubes of desired length, most preferably made of titanium, are retrieved by the automated gripper of the robot from the tube dispenser, moved to the laser welder and welded at the bottom, moved to the loader-filler and loaded with a predetermined mass to be contained inside the tube, inspected to insure proper filling, returned to the laser welder for welding the top of the tube, inspected to insure weld integrity, and then moved to the output receiver and released.

According to a particularly preferred application of the invention, the subject system and method are used to produce brachytherapy seeds for localized radiation treatment of cancer cells. When producing brachytherapy seeds, the contained mass preferably comprises a plurality of spheres coated or impregnated with a radionuclide, or a gel or gelable material containing a radionuclide.

BRIEF DESCRIPTION OF THE DRAWINGS

The invention is further described and explained in relation to the following figures of the drawings, wherein:

FIG. 9 is a simplified elevation view, partially broken away and partially in cross-section, of a titanium tube of the type that can be sealed and welded using the system of the invention;

FIG. 10 is a simplified elevation view, partially broken away and partially in cross-section, of a titanium tube containing five metal spheres and sealed at each end following laser welding to form a brachytherapy seed in accordance with a preferred method of the invention;

FIG. 11 is a simplified perspective view of an output receiver module of the tube filling and sealing apparatus of the invention.

DETAILED DESCRIPTION OF THE PREFERRED EMBODIMENTS

Figure 1:
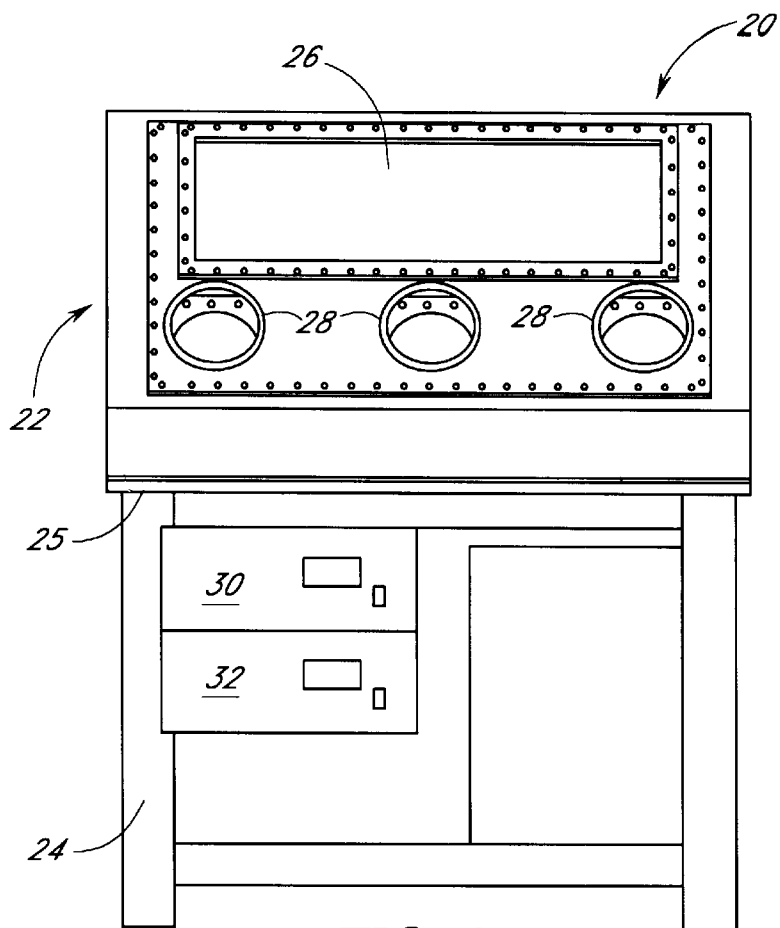
FIG. 1 is a simplified front elevation view of the primary enclosure for the manufacturing system of the invention.

It is to be understood that the invention disclosed herein is broadly directed to a system and method for sealing metal tubes by the use of a laser welding apparatus having multiple (two or more) heads for directing laser beams substantially simultaneously against the tube from more than one direction. Using the system and method of the invention, metal tubes of a predetermined length and diameter are sealed by sequentially welding the opposite ends of the tube. Each end weld is achieved through the application of laser beams directed against the outside tube wall, either simultaneously or nearly simultaneously, from laser heads spaced around the periphery of the tube. Desirably, a single beam of light emanating from a laser is split and a portion of the beam is directed through each of a plurality of fiber optic conductors to a different laser welding head. The beams exiting the multiple heads are directed against the metal tube, or target, and converge on the target from different directions, impacting the outside wall of the tube at positions near the tube ends that desirably define a plane generally transverse to the longitudinal axis through the tube. This simultaneous use of multiple laser welding heads to seal the open ends of a vertically oriented metal tube is believed to be disclosed herein for the first time.

In many instances, the metal tube is advantageously supported in a vertical or substantially vertical position during welding. We have discovered that when the open bottom end of a metal tube is being welded, the application of laser-directed light beams against points disposed slightly above the tube end and at two or more spaced-apart points on its periphery can cause the downwardly extending end of the tube wall to be drawn upwardly and inwardly, effectively sealing off the lower end of the tube. Similarly, when the laser beams are directed against the tube wall at circumferentially spaced points near and approximately equidistant from the upper end, the tube end is drawn downwardly and inwardly, effectively sealing off the upper end of the tube.

After the bottom end of the tube is welded, a solid, liquid, gaseous or gelled mass, or a combination of thereof, can be placed or otherwise loaded inside the tube and the top end is then welded to seal the mass inside the tube. The tube is desirably purged with a flow of inert gas prior to and during welding.

The present invention is believed to be useful for sealing metal tubes of various lengths and diameters, made of various metals, and for many different types of uses. The metal tubes can have many different types of contained masses, and welding of the tube ends can be achieved using different power lasers, and with different numbers and placement of laser heads, a particularly preferred utility for the invention is the production of brachytherapy seeds having a radionuclide as the contained mass.

The detailed description as set forth below is primarily directed to the preferred embodiment of the invention as used in producing brachytherapy seeds. Brachytherapy seeds as disclosed herein are typically about the size of a grain of rice and comprise a sealed metal tube, most preferably titanium, containing a radionuclide. The radionuclide can be coated on or impregnated into solid bodies, such as spheres, that are loaded into the axial bore of the metal tubes after one end is welded. Alternatively, the radionuclide can be encapsulated as either a liquid or gel within the metal tube, and if desired, can first be incorporated into another containment device or structure such as a plastic shell or sleeve prior to loading it into a metal tube. The brachytherapy seeds can be inserted clinically into body tissue such as the prostate to irradiate surrounding tissue in the treatment of cancer or other maladies. The strength and period of the irradiation are controlled through judicious selection of the type and dosage of the contained mass of radionuclide. The use of one or more radioactive substituents, such as radioactive iodine, in producing brachytherapy seeds in turn necessitates the use of a manufacturing system and method that minimize the exposure of workers to harmful radiation.

Referring to FIG. 1, system 20 of the invention preferably comprises enclosure 22, which houses the SCARA robot and other related modules or subassemblies used in manufacturing brachytherapy seeds as are described in greater detail below. Enclosure 22 should provide a protective environment for radiological containment during the manufacture of brachytherapy seeds, including radiological shielding, and should operate at a negative pressure with respect to the surrounding room to ensure operator safety. Enclosure 22 is preferably supported on frame or stand 24 by base plate 25 and comprises a work station with a window 26 and glove ports 28 on each side. Enclosure 22 is preferably made of stainless steel. Enclosure 22 should have conventional connectors (not shown) for electricity, compressed air and inert gas. Connections should also be provided to a computer operating system, preferably comprising first and second control computers 30, 32, and for fiber optic cabling as discussed below in relation to FIGS. 2, 5, 8 and 12.

The entire system should operate at a negative pressure with respect to the surrounding room to provide a safe working environment for the operator. Exhaust air should be vented to the facility exhaust air handling system with filtering to remove gaseous and radioactive particles. A conventional airlock (not shown) is desirably provided. Pressurization of the airlock must be negative to the surrounding room. Airlock pressurization is preferably monitored and verified by a magnahelic gauge.

Figure 2:
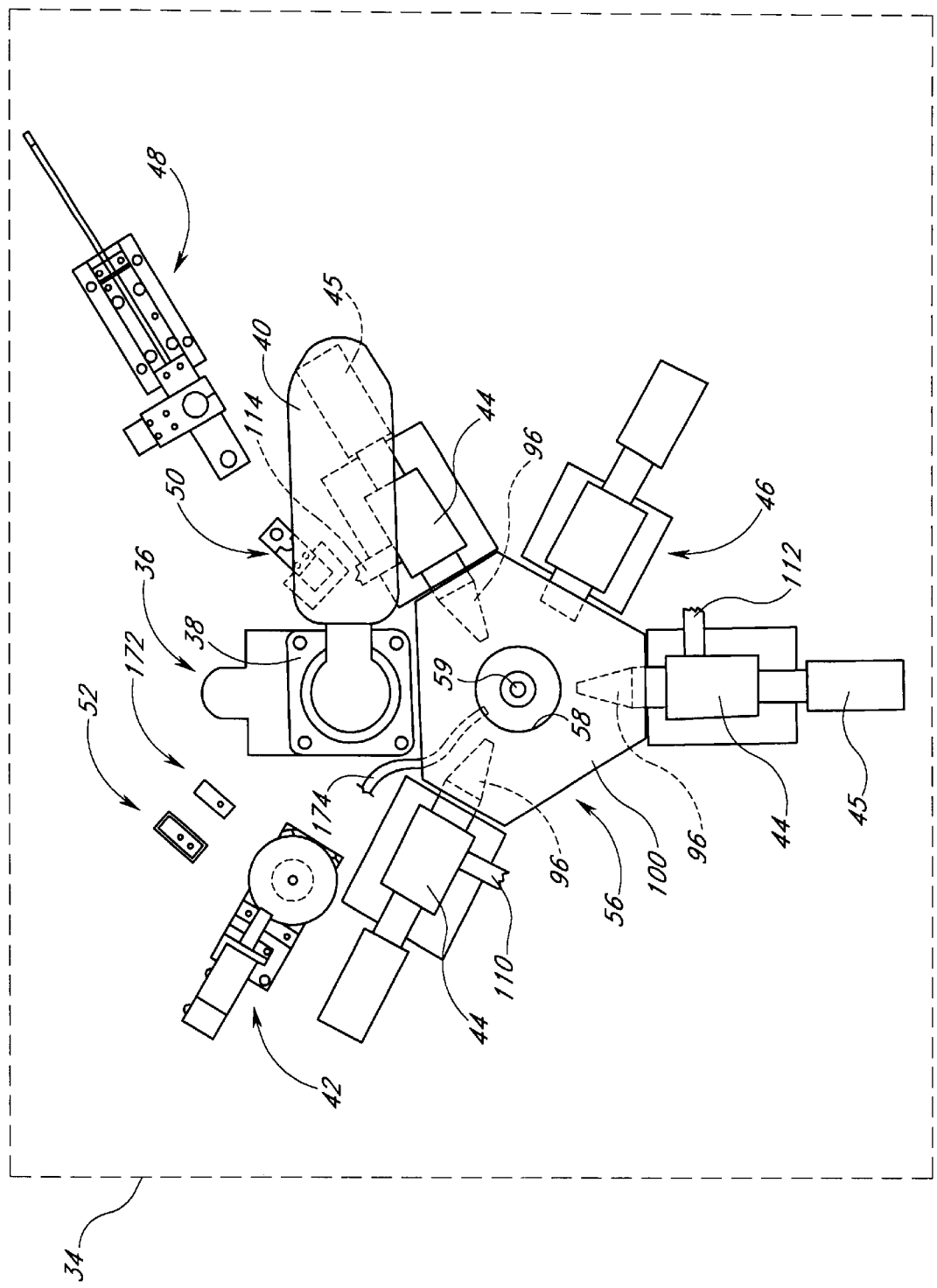
FIG. 2 is a simplified top plan view of the tube filling, sealing and inspection apparatus for the manufacturing system of the invention.

Referring to FIG. 2, dashed line 34 generally represents the substantially rectangular boundaries of base plate 25 of enclosure 22 as described above. FIG. 2 depicts a simplified plan view, without cables, etc., showing a preferred arrangement of most of the various modules or subassemblies used within the method of the invention to make, for example, brachytherapy seeds. SCARA robot 36 is preferably located so that most of its functions can be performed simply by moving support arm 40 relative to stationary base 38. Robots 36 preferred for use in the subject apparatus and in the manufacture of brachytherapy seeds in accordance with the preferred method of the invention use pre-programmed instructions to retrieve a metal tube, most preferably made of titanium, and present the tube to a series of pre-set locations where the tube is welded at the bottom end, loaded with spheres, welded at the top end, inspected and deposited for storage. Robot 36 is preferably bolted inside enclosure 22.

Figure 4:
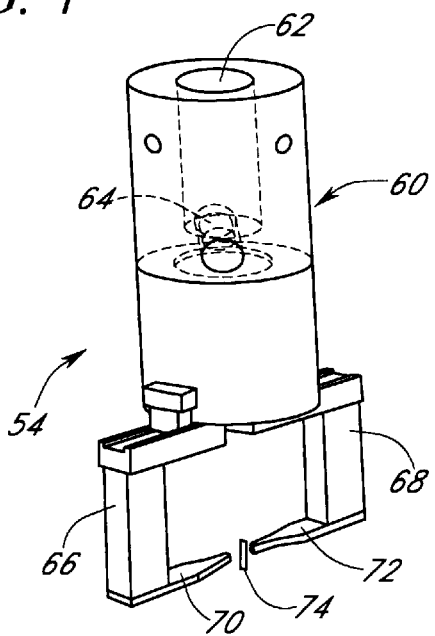
FIG. 4 is a simplified perspective view of the tube gripper module of the invention showing two opposed gripper fingers in the open position relative to a titanium tube disposed between them.
Figure 4A:
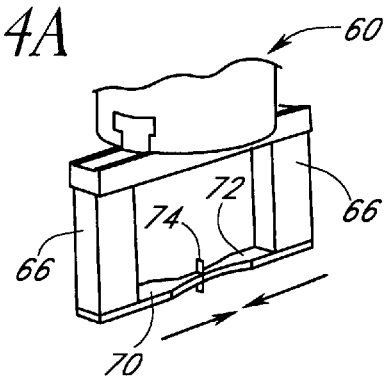
FIG. 4A is a detail view of the lower portion of the tube gripper module as shown in FIG. 4, but with the two opposed gripper fingers drawn together to grip the titanium tube disposed between them.

Referring to FIGS. 1, 2, 4 and 4A, robot 36 preferably further comprises automated gripper 54 mounted beneath support arm 40, which is preferably articulated, with two segments independently rotatable in a horizontal plane and capable of positioning automated gripper 54 over any point within the working zone inside enclosure 22. Automated gripper 54 preferably comprises body 60 clamped to a spindle from support arm 40 that is inserted into receptacle 62. Support arm 40 desirably enables body 60 to be selectively elevated, lowered, or rotated as desired. Opposed gripper fingers 66, 68 having opposed finger inserts 70, 72 are preferably slidably mounted on the underside of body 60 and are controllable, preferably pneumatically through valve 64, so as to grip and support a metal tube 74, as shown in FIGS. 4 and 4A, and then subsequently release it at an appropriate time in accordance with the method of the invention. Automated gripper 54 is preferably constructed and installed so as to provide the necessary clearance relative to the other modules or subassemblies mounted inside enclosure 22. Robot controller 30 communicates with robot 36, relaying programmed instructions to robot 36 to guide support arm 40, gripper fingers 66 and finger inserts 70, 72 (FIGS. 4, 4A) sequentially through a predetermined series of motions at various locations corresponding to the different work stations inside enclosure 22.

Referring again to FIG. 2, mounted around robot 36 are tube dispenser 42, laser heads 44, laser alignment cameras 45, inspection camera 46, sphere loader 48, sphere checker 50, output receiver 52 and release sensor 172. Although three laser heads 44 are shown in FIG. 2 in accordance with a preferred embodiment of the invention, it will be appreciated that for some applications and metal tube diameters, a single laser head may be sufficient for closing the tube ends in a satisfactory manner. In general, however, it is believed that better welds and better results are achieved using a plurality of circumferentially spaced laser heads 44 that each contribute to making the weld.

Figure 3:
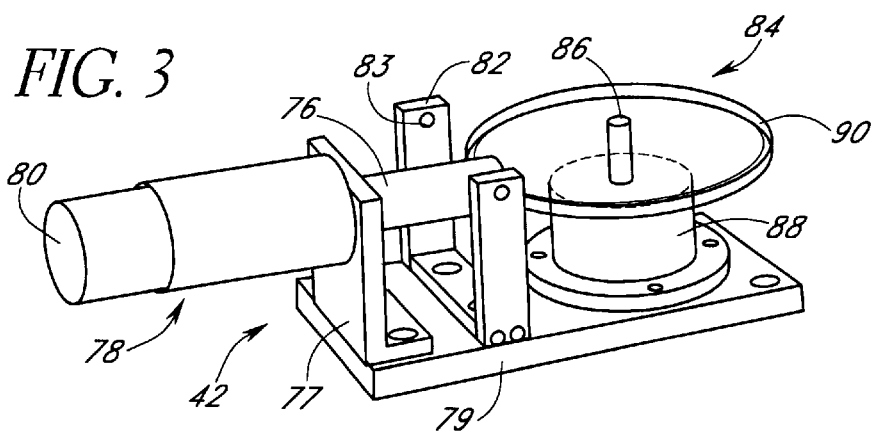
FIG. 3 is a simplified perspective view of the tube dispenser module of the tube filling and sealing apparatus.
Figure 3A:
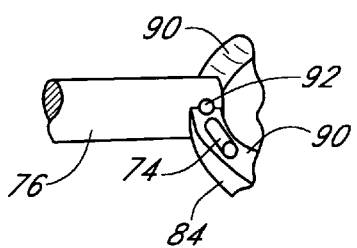
FIG. 3A is an enlarged, detail perspective view of a portion of the flip tube that is part of the tube dispenser module of FIG. 3 and is used in recovering a metal tube from a track at the top of a vibratory bowl.
Figure 3B:
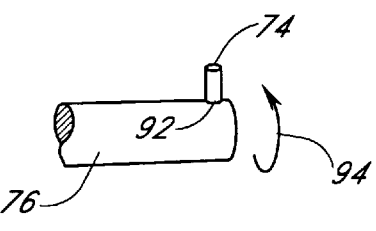
FIG. 3B is an enlarged, detail perspective view showing the flip tube of the tube dispenser module after it has been rotated approximately 90 degrees, from a substantially horizontal position to a substantially upright position to facilitate pick-up by the automated gripper assembly.

Referring to FIGS. 3, 3A and 3B, tube dispenser 42 is desirably used to present metal tubes 74 in an upright position for retrieval by automated gripper 54 of robot 36 as described above. Tube dispenser 42 preferably comprises a mounting plate 79 securable in a fixed position relative to enclosure 22 and robot 36, previously described, at least one rotary bracket 77 supporting rotator housing 78, flip tube 76, pneumatic cam 80, sensor assembly 82 and vibratory bowl 84 connected by shaft 86 to vibratory motor 88.

Referring to FIG. 9, which is not drawn to scale, metal tubes 74 used in practicing the preferred embodiments of the invention as described herein are preferably made of titanium because of its resistance to corrosion and its widespread acceptance for use in devices and structures that are implantable in the human body. It will be appreciated, however, that other metals and alloys can also be used within the scope of the invention provided that such metals perform satisfactorily in the intended application and are approved for such use. For purposes of manufacturing brachytherapy seeds, metal tubes 74 are preferably open-ended titanium tubes having a cylindrical cross-section. When welded, the tubes are desirably about 4.5 mm long, have an outside diameter of about 0.8 mm and a wall thickness of about 0.05 mm.

When metal tubes 74 are dumped into vibratory bowl 84, they migrate upward to annular, semi-cylindrical, circumferentially extending track 90, where they are transported to cylindrical aperture 92 of flip tube 76, as is visible in FIG. 3A. When a metal tube 74 is seated inside aperture 92, flip tube 76 is rotated upwardly by pneumatic cam 80 as indicated by arrow 94 until metal tube 74 is substantially vertical. Although other similarly effective mechanical configurations can used, the tube dispenser should be capable of consistently presenting a single metal tube for retrieval by automated gripper 54. Optical sensors located in sensor assembly 82 and containing an LED pair 83, 85 are preferably adapted to signal the robot controller once metal tube 74 is vertically oriented and ready for pick-up by automated gripper 54.

Figure 8:
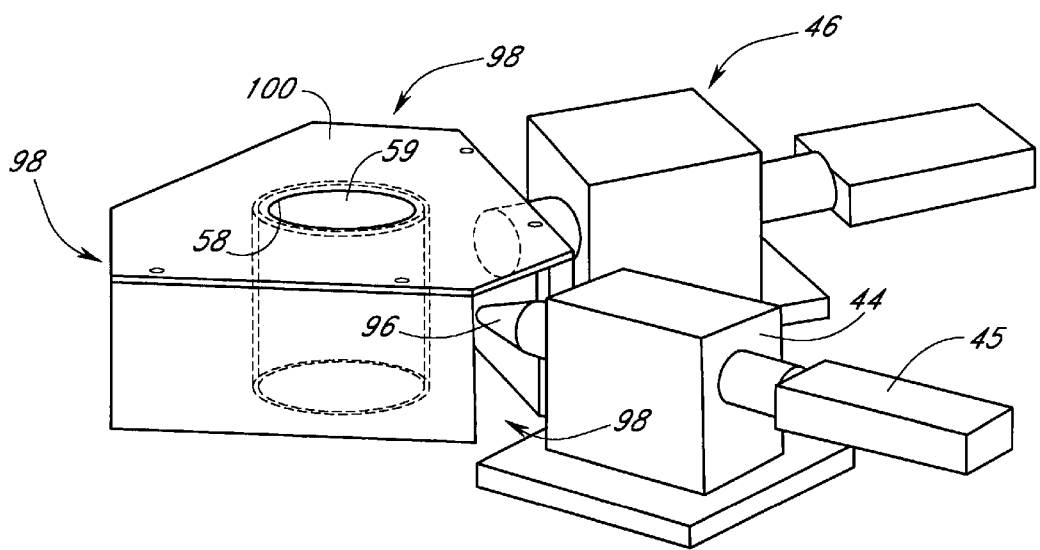
FIG. 8 is a simplified perspective view of the welding and inspection module of the tube filling and sealing apparatus of the invention, showing the positional relationship between one of the laser welder heads and the welding and inspection well.

Referring to FIG. 2, three laser heads 44 are preferably mounted at substantially equally spaced intervals of about 120° around the major arc traversed by swivel arm 40 of robot 36. Referring to FIGS. 2 and 8, tips 96 of laser heads 44 preferably extend radially inward through sidewall portals 98 of hood 56, and are directed so that laser beams emanating from tips 96 of each laser head 44 converge at the center of welding zone 59. Cylinder 58 defining welding zone 59 is desirably transparent and lighted to facilitate laser welding and subsequent inspection by camera 46. Only one laser head 44 is shown for illustrative purposes in FIG. 8 but it will be understood that other laser heads are similarly mounted relative to the other two portals 98 in hood 56. At each stage of the method of the invention where welding of a metal tube is desired, swivel arm 40 of robot 36 is desirably positioned by the robot controller over robot access aperture 58 in the substantially horizontal upper surface 100 of hood 56, and the metal tube is lowered by automated gripper 54 (FIGS. 4 and 4A) so that the metal tube to be welded is properly positioned in welding zone 59, best seen in FIG. 2.

Figure 5:
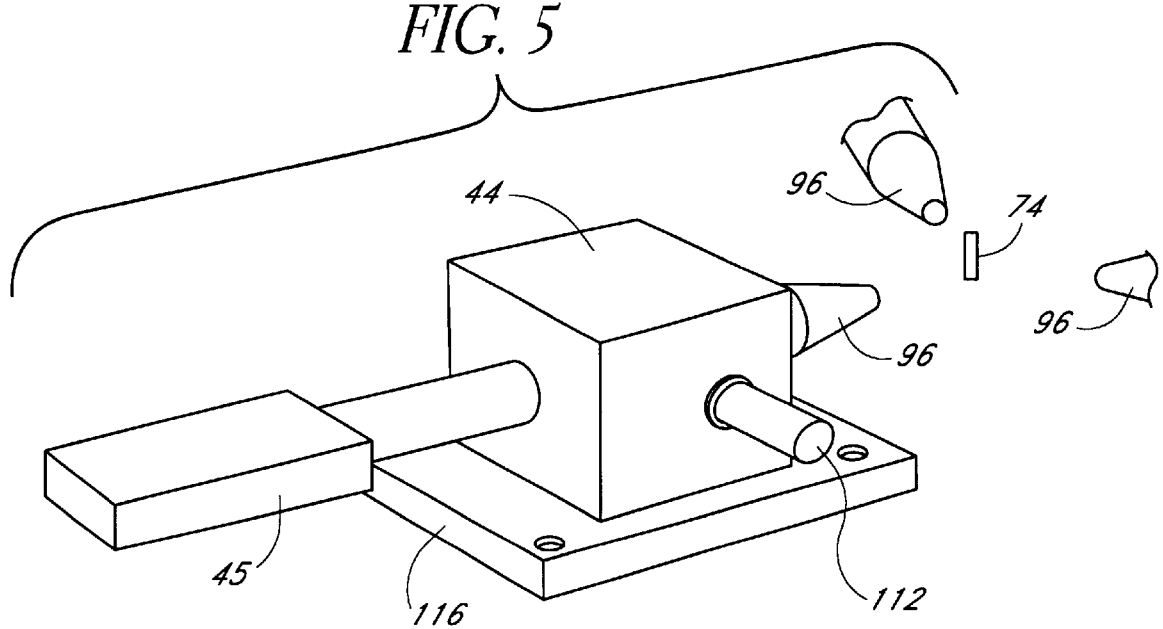
FIG. 5 is a simplified perspective view of one of the three laser welder heads of the tube filling and sealing apparatus, with broken-away head portions of two other laser welder heads also being shown to depict their position relative to a metal tube, the tube being shown here in dashed outline.
Figure 5A:
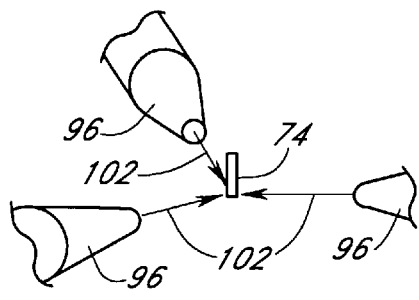
FIG. 5A is a simplified diagrammatic view showing three laser welder heads welding the bottom of a metal tube prior to loading the tube.
Figure 5B:
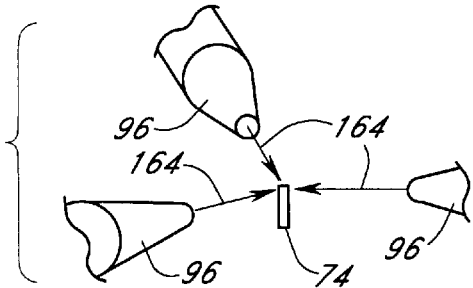
FIG. 5B is a simplified diagrammatic view as in FIG. 5A but showing welding the top of the metal tube after the tube is loaded.

FIG. 5 is simplified perspective view showing one laser head 44 mounted on base 116, including tip 96 and fiber optic cable 112, in relation to tips 96 of the other two laser heads 44 and metal tube 74. FIGS. 5, 5A and 5B each depict a metal tube positioned for welding where laser beams emanating from each of tips 96 of laser heads 44 will converge. FIG. 5A is a simplified illustration of a metal tube 74 positioned so that laser beams 102 from each of tips 96 will converge near the bottom of the tube, thereby sealing the lower end with a weld. We have discovered that when a small diameter, open metal tube is supported in a vertical position, the controlled application of one or more laser beams to the side wall of a small diameter metal tube a short distance from the bottom end of the tube causes the metal to be drawn inwardly and upwardly to produce a seal across the previously open end. Similarly, FIG. 5B is a simplified illustration showing a metal tube 74 positioned so that laser beams 102 from each of tips 96 will converge near the top of the tube, thereby also sealing its upper end with a weld. According to a preferred embodiment of the invention, between the time that the bottom tube end is sealed as shown in FIG. 5A and the time that the top tube end is sealed as shown in FIG. 5B, robot 36 (FIG. 2) will retract metal tube 74 from welding zone 59 and move it to another module or subassembly within enclosure 22 (FIG. 1) so that a mass to be contained inside metal tube 74 can be loaded into the open, top end, and will then return metal tube 74 to welding zone 59 to effect the final weld. Inert gas, preferably helium because it is lighter than air, is introduced within the welding zone as through tube 174 (FIG. 2) to reduce oxidation of the metal during the weld. The timing of gas purges is desirably computer controlled so that they only occur during welding.

According to another preferred aspect of the invention, because some of the purge gas is sealed inside the tubes by the welds, any subsequent leakage of the purge gas can be monitored during later inspection using a helium mass spectrometer to help identify welds lacking complete integrity.

Figure 12:
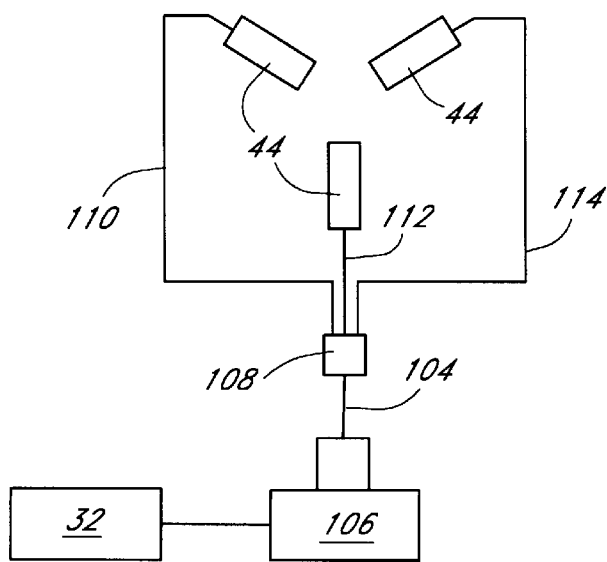
FIG. 12 is a simplified schematic illustrating the generation, splitting and direction of a laser beam to the respective laser welding heads as are described below in relation to FIGS. 2, 5 and 8.

FIG. 12 is a schematic showing in simplified form how a single laser beam 104 generated by laser 106 is divided by beam splitter 108 into three separate, substantially identical, lower power beams that are transmitted through fiber optic cables 110, 112, 114 to laser heads 44. Laser heads 44 are preferably powered by a Neodymium-doped Yttrium Aluminum Garnet (Nd:YAG) laser 106 are preferably used to weld the eds of a metal tube 74 so as to seal a mass inside the cylindrical bore of the tube between the welded ends. Laser 106 and laser heads 44 are desirably capable of interfacing to a variety of fiber optic cable sizes and lengths. Laser heads 44 will desirably have several laser output-sharing modes including but not limited to the number of outputs, energy sharing and time sharing.

Figure 6:
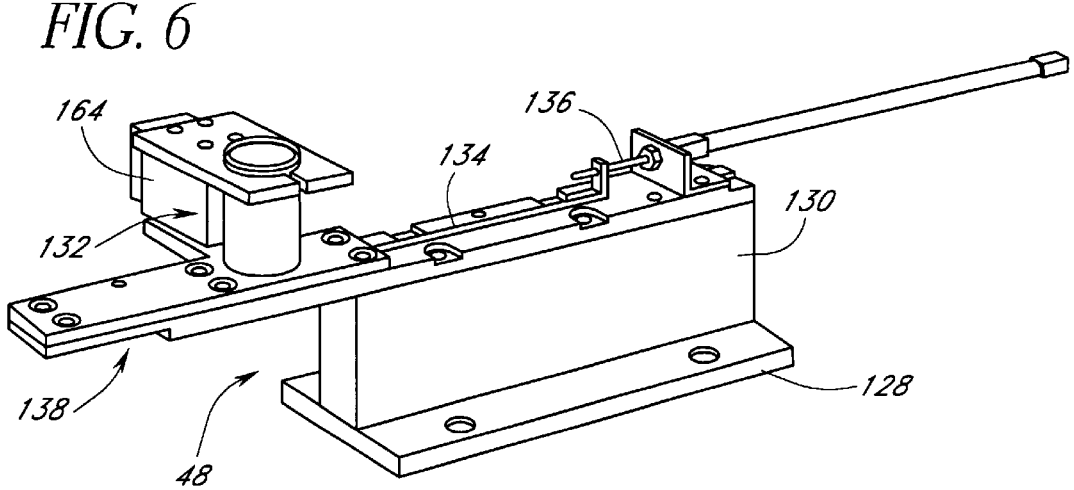
FIG. 6 is a simplified perspective view of the sphere loader module of the tube filling and sealing apparatus of the invention.

Referring again to FIG. 2, laser heads 44 preferably utilize an auxiliary system for aiming the laser while the main beam is off line. Closed circuit television cameras (CCTV) 45 having at least 50× magnification and cross-hairs for direct observation of the welding zone 59 through laser heads 44 are also desirably provided. The CCTV system should be capable of aligning and/or verifying alignment of titanium tubes 74 to the beam. An ENET module will desirably serve as the analog/digital interface between the robot controller 30 (FIG. 1) and laser 106 to facilitate laser communications and the independent firing of the laser. Referring to FIGS. 2, 8, and 10, vision guide system 46 of system 20 is preferably used for inspecting bottom weld 120 and top weld 126 of metal tubes 74 used to make brachytherapy seeds 170. Vision guide system 46 desirably interfaces with software that is used to program the operation of robot 36. Vision guide system 46 will desirably include a video camera, adjustable diffused lighting, appropriate lenses and mounting apparatus and a computer. During inspection of bottom weld 120, metal tube 74 is preferably rotated a full 360° by robot 36 while still inside welding zone 59. If weld 120 is not satisfactory, robot 36 is desirably programmed to reposition tube 74 over a rejection vial, discussed below, and release it. Following completion of the inspection of bottom weld 120 with an acceptable result, metal tube 74, still having an open top end, is repositioned by robot 36 beneath dispensing arm 138 of sphere loader 48 (FIG. 6).

As mentioned above, the mass to be contained inside metal tubes 74 can take many different forms, depending upon various factors such as availability, cost, efficiency and reliability of manufacture, and particularly, upon the intended use. In manufacturing brachytherapy seeds according to the preferred embodiment disclosed herein, the mass to be sealed inside metal tubes 74 includes a plurality of small-diameter metal spheres coated with a radioactive component having a level of radioactivity and half-life suitable for producing a desired dosage.

The module or subassembly used to install the spheres inside the cylindrical bore of metal tubes 74 is sphere loader 48, which is further described and explained with reference to FIGS. 2, 6 and 10. Sphere loader 48 of the invention is used to load radiolabeled microspheres 122, visible in FIG. 10, into metal tubes 74, each having a previously welded bottom end 120. Sphere loader 48 must be capable of consistently and reliably dropping a predetermined number, preferably five, radiolabeled microspheres 122 into the pre-welded (bottom only) metal tubes 74. Sphere loader 48 preferably comprises base plate 128 for use in mounting the module in a desired position relative to robot 36, body 130, sphere dispensing cylinder 132, sphere loading track 134 and sphere loading slide 136, which is desirably pneumatically actuated. Spheres 122 descend through a gate in the bottom of cylinder 132 and fall into track 134. Track 134 is preferably configured to accept only a predetermined number of spheres 122, in this case five. Slide 136 is then pneumatically actuated to push spheres 122 forward along track 134 until they drop through an aperture (not visible) in the underside of dispensing arm 138 into the upwardly facing, open end of metal tube 74. Sphere loader 48 should accommodate radiolabeled microspheres 122 having a diameter of about 0.64 mm, and in any event, having a diameter that is less than the internal diameter of metal tube 74. Radiolabeled microspheres are disclosed in U.S. Pat. No. 5,342,283 to Good.

Figure 7:
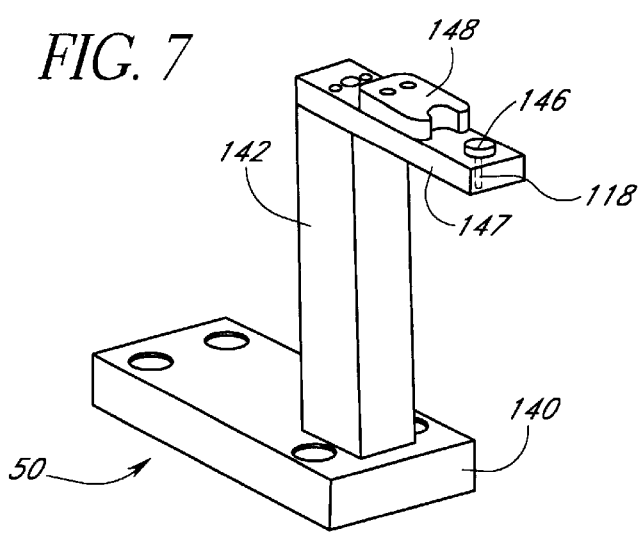
FIG. 7 is a simplified perspective view of the sphere checker module of the tube filling and sealing apparatus of the invention.

Once spheres 122 are loaded into a metal tube 74, robot 36 again repositions metal tube 74 below arm 147, elevated above base 140 on riser 142 of sphere checker module 50, shown in FIGS. 2 and 7. Downwardly extending pin 118 and button 146 are mounted in arm 147 in fixed relation to each other so that they can slide up and down in unison relative to arm 147. As tube 74 is raised upwardly under arm 147 by robot 36, pin 118 desirably enters the open top end of metal tube 74 and contacts the topmost sphere 122 in tube 74. Depending upon the number of spheres 122 inside tube 74, button 146 is elevated to a greater or lesser distance above the top surface of arm 147. The filled tubes 74 are accepted or rejected based on the readout of photoelectric go/no-go sensor 148, which is preferably calibrated to accept tubes 74 loaded with five microspheres 122 and reject tubes 74 loaded with more or fewer than five microspheres 122.

Following loading and checking of metal tube 74, robot 36 desirably repositions tube 74 inside welding zone 59 so that beams 164 from tips 96 of laser heads 44 are directed against the outside walls of tube 74 near its upper end as shown in FIG. 5B. Activation of laser 106 and laser heads 44 (FIGS. 2, 5 and 12) by computer 32 (FIG. 1) creates top weld 126 (FIG. 10) to produce finished brachytherapy seed 170. Following the completion of top weld 126 to form seed 170, robot 36 rotates seed 170 a full 360° while still cylindrical space 58 to permit examination of top weld 126 by the camera in module 46 to evaluate weld integrity. Following this inspection, robot 36 repositions seed 170 over output receiver 52.

Referring to FIG. 11, output receiver 52 preferably comprises base plate 150 that houses vial holder 152. Vial holder 152 has recesses 154, 156 for at least two separate vials for placement of the brachytherapy seeds 170. Robot 36 as previously described is programmed to deposit brachytherapy seeds that pass all inspections into one vial and all seeds that fail any inspection into another vial. If desired, additional vials can be provided for depositing seeds that fail inspection at a particular stage of the manufacturing process.

Because of the relatively light weights of the materials being handled by the apparatus of the invention, most metal parts of the apparatus are desirably fabricated from aluminum. Those parts that are repeatedly recycled during the manufacturing process or that directly contact metal tubes 74 or microspheres 122 are desirably made of stainless steel to reduce wear.

Seeds 170 should be substantially free of foreign material, particle, dents or bends. The welds should be silver in color, without discoloration, sharp edges, significant bulges, holes or incomplete fusion in the weld joint where the weld meets the tube surface. The outer diameter of finished seeds 170 is approximately 0.8 mm and the length is preferably about 4.5 mm. Finished seeds are desirably maintained in vials that are tightly capped and free of dirt, debris and contaminants. The product is stored in an environmentally controlled area, in locked enclosures and segregated by run number. Each vial is labeled with the product name, run number and code number.

According to the method of the invention, with reference to FIGS. 1–12, clean, pre-cut metal tubes 74, preferably made of titanium, are dispensed individually to a SCARA robot 36, which positions and sequentially advances them through the various work stations as needed for the manufacture of the brachytherapy seeds 170. Steps of the subject method desirably include continuously feeding and successively orienting in a vertical position a series of metal tubes 74 using a tube dispensing module 42, grasping a metal tube 74 using gripping fingers 66, 68 and finger inserts 70, 72 attached to robot 36 to facilitate repositioning metal tube 74 as needed to complete the process while under the control of a computer 30, welding the bottom end 120 of tube 74 using a plurality of laser heads 44 having beams in substantially the same horizontal plane controlled by computer 32 and directed so as to substantially converge in a predetermined region in a welding zone 59 in which tube 74 is supported, inspecting weld 120, loading a predetermined mass (as, for example, five radioactive microspheres 122) into bottom-welded tube 74, verifying proper loading of the mass inside tube 74, repositioning loaded tube 74 in welding zone 59 to produce top weld 126, thereby forming brachytherapy seed 170, inspecting top weld 126, and depositing the finished seed 170 in the appropriate vial location in output receiver 52. A release sensor 172, desirably located near output receiver 52, as seen in FIG. 2, preferably verifies that seed 170 has in fact dropped from automated gripper 54 before robot 36 commences the next cycle.

In addition to the visual weld inspections performed during the manufacturing process as described above, additional testing is desirably performed on products intended for use in applications such as brachytherapy seeds. Such tests include, for example, a radioassy using an I-125 Seed Standard traceable to the National Institute of Standards and Technology (NIST). The seeds are also desirably subjected to a radionuclidic purity test, performed using a high performance germanium detector (HPGe) calibrated with standards also directly traceable to NIST.

With the multi-directional laser system and method disclosed herein, the pulse targets tube 74 near the bottom or top open end, respectively. Precision in the position on metal tube 74 targeted by laser heads 44 and the pulse energy are important to the welding process. This single laser pulse technique eliminates the need to rotate either tube 74 or the welding implement during the welding process. This new laser welding process is a significant benefit to effective automation and the enhanced product quality.

Other alterations and modifications of the system, apparatus and method disclosed herein will likewise become apparent to those of ordinary skill in the art upon reading this disclosure, and it is intended that the scope of the invention be limited only by the broadest interpretation of the appended claims to which the inventors are legally entitled.

What is claimed is:

1. An automated brachytherapy seed production system comprising a radiation safety enclosure having disposed therein a robotically operated tube gripper, a tube dispenser, a radioactive source loader, and a multiple-directional laser welder, wherein the radioactive source loader further comprises a cylinder through which a plurality of radiolabeled microspheres are controllably discharged, and a slide that is actuatable to load the discharged microspheres into a tube having a welded bottom, said tube being supported by the tube gripper.

2. The system of claim 1, further comprising a radioactive source check module disposed inside the enclosure.

3. The system of claim 1, further comprising an inspection module disposed inside the enclosure.

4. The system of claim 1, further comprising an output receiver module disposed inside the enclosure.

5. The system of claim 1, further comprising at least one programmable electronic controller.

6. The system of claim 1 wherein the multi-directional laser welder has a plurality of heads, each head receiving a beam through a separate fiber optic cable from a common laser beam source and each head being positioned to direct a laser beam from a different direction into a common welding zone.

7. The system of claim 1 wherein the enclosure further comprises a welding zone and means for purging the welding zone with an inert gas.

* * * * *